(12) United States Patent
Parker et al.

(10) Patent No.: US 10,648,014 B2
(45) Date of Patent: May 12, 2020

(54) DEGRADATION RESISTANT PEPTIDE BASED BIOSENSORS

(71) Applicant: Purdue Research Foundation, West Lafayette, IN (US)

(72) Inventors: Laurie L Parker, Minneapolis, MN (US); Robert John Schuster, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 39 days.

(21) Appl. No.: 15/309,002

(22) PCT Filed: Apr. 29, 2015

(86) PCT No.: PCT/US2015/028236
§ 371 (c)(1),
(2) Date: Nov. 4, 2016

(87) PCT Pub. No.: WO2015/171395
PCT Pub. Date: Nov. 12, 2015

(65) Prior Publication Data
US 2017/0101664 A1 Apr. 13, 2017

Related U.S. Application Data

(60) Provisional application No. 61/988,739, filed on May 5, 2014.

(51) Int. Cl.
*C12Q 1/48* (2006.01)

(52) U.S. Cl.
CPC ......... *C12Q 1/485* (2013.01); *G01N 2440/14* (2013.01)

(58) Field of Classification Search
CPC ............................ C12Q 1/485; G01N 2440/14
See application file for complete search history.

(56) References Cited

U.S. PATENT DOCUMENTS

| | | | | |
|---|---|---|---|---|
| 5,834,592 A | * | 11/1998 | Reed | C07K 14/44 530/350 |
| 2003/0175290 A1 | * | 9/2003 | Renner | A61K 39/0005 424/186.1 |
| 2006/0154863 A1 | * | 7/2006 | Skubatch | C07K 14/005 514/18.3 |
| 2007/0292898 A1 | * | 12/2007 | Buist | C07K 14/70571 435/7.21 |
| 2013/0231265 A1 | | 9/2013 | Parker et al. | |

OTHER PUBLICATIONS

Placzek et al. "A peptide biosensor for detecting intracellular Abl kinase activity using matrix-assisted laser desorption/ionization time-of-flight mass spectrometry," Anal Biochem. Oct. 7, 2009, vol. 397, pp. 1-13 [originally pp. 73-78], Elsevier B.V., Amsterdam, NL.
Yang et al. "A multiple reaction monitoring (MRM) method to detect Bcr-Abl kinase activity in CML using a peptide biosensor," PLoS One, Feb. 20, 2013, vol. 8, e56627, pp. 1-10, PLOS ONE, San Francisco, CA, US.
Dayamanti et al. "Fluorescence lifetime imaging of biosensor peptide phosphorylation in single live cells," Angew Chem Int Ed Engl. Feb. 28, 2013, vol. 52, pp. 1-9 [originally pp. 3931-3934], Wiley, Weinheim, DE.
Lipchik et al. "A peptide-based biosensor assay to detect intracellular Syk kinase activation and inhibition," Biochemistry. Sep. 12, 2012, vol. 51, pp. 1-20 [originally pp. 7515-7524], ACS Publications, Washington, DC, US.
Tang et al. "Detection of early Abl kinase activation after ionizing radiation by using a pepide biosensor," Chembiochem Feb. 14, 2012, vol. 13, pp. 1-18 [originally pp. 665-673], American Research Institute for Policy Development, Madison, WI, US.
International Searching Authority, International Search Report for PCT/US2015/028236, World Intellectual Property Organization, 4 pages, dated Nov. 13, 2015.
International Searching Authority, Written Opinion of the International Searching Authority for PCT/US2015/028236, World Intellectual Property Organization, 7 pages, dated Nov. 13, 2015.

* cited by examiner

*Primary Examiner* — Susan E. Fernandez
(74) *Attorney, Agent, or Firm* — Purdue Research Foundation; Liang Zeng Yan

(57) ABSTRACT

Disclosed are compositions and methods for measuring tyrosine kinase activity using degradation resistant biosensors comprising a reporter sequence, a target sequence, and a transduction sequence. In certain embodiments, the invention includes a biosensor comprising a peptide comprising a reporter sequence, i.e., an amino acid sequence including a tyrosine residue that can be phosphorylated by a tyrosine kinase. In certain embodiments, a biosensor comprises a reporter sequence configured to resist degradation from proteases, a targeting sequence coupled to the reporter sequence and configured to bind to a protein interaction domain of a kinase, and a transduction sequence coupled to the targeting sequence.

15 Claims, 13 Drawing Sheets
Specification includes a Sequence Listing.

DEGRADATION RESISTANT PEPTIDE BASED BIOSENSORS

CROSS-REFERENCE TO RELATED APPLICATIONS

The present U.S. patent application claims the priority benefit of PCT International Application Serial No. PCT/US2015/028236 filed on Apr. 29, 2015 and U.S. Provisional Patent Application Ser. No. 61/988,739, filed May 5, 2014, the contents of which are hereby incorporated by reference in their entirety into this disclosure.

STATEMENT GOVERNMENT INTEREST

This invention was made with government support under CA127161 and CA160129 awarded by the National Institutes of Health. The government has certain rights in the invention.

SEQUENCE LISTING

Incorporated by reference in its entirety herein is a computer-readable sequence listing electronically filed with this application.

TECHNICAL FIELD

This disclosure relates to degradation resistant peptide biosensors and in particular to degradation resistant peptides for selective measurement of kinase activity.

BACKGROUND

This section introduces aspects that may help facilitate a better understanding of the disclosure. Accordingly, these statements are to be read in this light and are not to be understood as admissions about what is or is not prior art.

Dysregulation of normal cellular signaling events has been attributed to a variety of diseases most notably cancer. Chronic myeloid leukemia (CML) is a hematological malignancy, characterized by unregulated growth of myeloid cells in the bone marrow, and their accumulation in the bloodstream. Expression of the Bcr-Abl oncogene is the primary driver in CML. Bcr-Abl is encoded on the mutant Philadelphia chromosome which arises from the translocation of chromosomes 9 and 22. This translocation involves the replacement of an autoinhibitory domain portion of the N-terminus of Abl with the Breakpoint-cluster-region (Bcr) protein. The expression of this fusion gene results in a protein product with constitutive tyrosine kinase activity.

The small molecule drug imatinib mesylate (Gleevec®) directly targets and inhibits the Abl kinase, and thus has become a frontline treatment for CML. Many patients undergoing Gleevec treatment do very well for many years, while some patients do not respond at all. Over time, some patients develop imatinib resistance such as Bcr-Abl point mutations or up-regulation of other kinases. Unfortunately, clinical signs of resistant cells repopulating the bone marrow are often not evident until CML has reached blast crisis. Second generation drugs such as nilotinib and dasatinib offer additional therapeutic options to overcome drug resistance. Assays to measure the activity of Bcr-Abl in patient cells could improve the longevity and treatment options available to CML patients through earlier detection of drug resistance. Furthermore, assays that could be used to evaluate inhibitor pharmacodynamics in preclinical animal models would benefit kinase inhibitor development by enabling more thorough characterization of drug efficacy and response.

SUMMARY

The present invention relates generally to compositions and methods for assaying tyrosine kinase activity, and particularly to compositions of peptide substrates which include a degradation resistant amino acid sequence.

For the purposes of this disclosure, when an amino acid is written in upper case letters it signifies an 'L' amino acid or L-amino acid and when an amino acid is written in lower case letters it signifies a 'D' amino acid or D-amino acid. For the purposes of this disclosure the start of a peptide sequence is associated with the amino (N) terminus, and the end of a sequence is associated with the carboxy (C) terminus. All sequences are written N terminus to C terminus.

For the purposes of this disclosure, 'biosensor' refers to a synthetic peptide biosensor comprising at least one sequence domain that is degradation resistant by the use of D-amino acids, an amino acid sequence in reverse order, or both. As an example, an amino acid sequence consisting of L-amino acids using generic variables to represent amino acids would be 'ABCABC'. As an example, the previous amino acid sequence consisting of D-amino acids would be 'abcabc'. As an example, the previous L-amino acid sequence provided in reverse order would be 'CBACBA'. Finally as an example, the previous amino acid sequence provided as D-amino acids in reverse order would be 'cbacba'.

In certain embodiments, the invention includes a biosensor comprising a peptide comprising a reporter sequence, i.e., an amino acid sequence including a tyrosine residue that can be phosphorylated by a tyrosine kinase. In certain embodiments, the biosensor includes a reporter sequence that can be phosphorylated by Syk, Btk, one or more Src family tyrosine kinases, Jak2, ALK, or Abl. In certain embodiments, the reporter sequence comprises D-amino acids. In certain embodiments the reporter sequence is provided in reverse order. In certain embodiments, the reporter sequence comprises D-amino acids in a reverse order. In certain embodiments, the biosensor includes one or more additional functional elements. In some embodiments, the functional elements include an affinity tag to facilitate capture, isolation or immobilization of the biosensor, or a cleavable linker. In certain embodiments, the biosensor may include an affinity tag, such as biotin or a poly-His tag. In certain embodiments the biosensor may include a transduction sequence. In certain embodiments the transduction sequence is a cell penetrating peptide. In certain embodiments, the cell penetrating peptide may be Tat. In certain embodiments the transduction sequence comprises D-amino acids. In other embodiments, the transduction sequence is provided in reverse order. In certain embodiments, the transduction sequence may include D-amino acids in reverse order. In certain embodiments, the biosensor may include a cleavable linker, such as a photo-cleavable linker. The photo-cleavable linker may include, for example, a photo-cleavable amino acid analog such as beta(nitrophenyl)alanine. The photo-cleavable linker covalently links two other elements of the biosensor. For example, the reporter sequence may be linked to an affinity tagged peptide sequence and linked through a photo-cleavable linker to a transduction sequence. In other embodiments, the biosensor is designed to include photo-cleavable linker between the reporter sequence and a targeting sequence. In certain embodiments the affinity tag is linked to the reporter sequence, the reporter sequence is linked to a targeting sequence, and the targeting sequence is linked to the transduction sequence. In other embodiments the biosensor includes an affinity tag which is linked to a reporter sequence, the reporter sequence is linked to a cleavable linker, the cleavable linker is linked to a targeting sequence, and the targeting sequence is linked to a transduction sequence.

In certain embodiments, a biosensor comprises a reporter sequence configured to resist degradation from proteases, a targeting sequence coupled to the reporter sequence and configured to bind to a protein interaction domain, and a transduction sequence coupled to the targeting sequence.

In certain embodiments, a biosensor comprises a reporter sequence configured to resist degradation from proteases, a targeting sequence coupled to the reporter sequence and configured to bind to a protein interaction domain of a kinase, and a transduction sequence coupled to the targeting sequence.

In certain embodiments, a biosensor comprises a reporter sequence configured to resist degradation from proteases, a targeting sequence coupled to the reporter sequence and configured to bind to a protein interaction domain of a kinase, and a transduction sequence coupled to the targeting sequence and configured to resist degradation from proteases.

In certain aspects the biosensor further includes a cleavable linker between the reporter sequence and the targeting sequence. In certain aspects the cleavable linker is a photocleavable linker.

In certain aspects the biosensor further includes an affinity tag. In some embodiments the affinity tag is linked or coupled to the reporter sequence at the start or N-terminus. In certain aspects the affinity tag is a biotinylated lysine residue. The lysine residue may be an L-amino acid or a D-amino acid.

In certain aspects the reporter sequence is an amino acid sequence comprising D-amino acids. In other aspects, the reporter sequence is comprised completely of D-amino acids. In other aspects the reporter sequence is a reverse sequence of amino acids. In other aspects, the reporter sequence is an amino acid sequence in reverse order comprising D-amino acids.

In certain aspects, the targeting sequence is a protein interaction domain formed from a whole protein interaction domain or a fragment of a protein interaction domain. In other aspects the protein interaction domain or fragment thereof is from a kinase protein interaction domain. In certain aspects the targeting sequence is coupled or linked between the reporter sequence and a transduction sequence. In certain aspects the targeting sequence comprises L-amino acids. In other aspects, the targeting sequence may comprise D-amino acids.

In certain aspects the transduction sequence is an amino acid sequence comprising a cell penetrating peptide. In other embodiments the transduction sequence is an amino acid sequence comprising a fragment of a cell penetrating peptide. In other aspects the transduction sequence comprises D-amino acids. In other aspects, the transduction sequence consists of D-amino acids. In other aspects the transduction sequence is an amino acid sequence in reverse order. In other aspects the transduction sequence comprises a D-amino acid sequence in reverse order.

In certain aspects, a method is provided for quantifying the enzymatic activity of a kinase including providing a sample including at least one recombinant kinase of interest, cell extract having a kinase of interest, or live cell having a kinase of interest, contacting the sample with a biosensor including a cleavable linker coupled between a reporter sequence and a targeting sequence configured to interact with the protein interaction domain of the kinase of interest, cleaving the cleavable linker on the biosensor, collecting the reporter sequence, and quantifying phosphorylation of the reporter sequence as a surrogate for kinase enzymatic activity. In certain aspects the reporter sequence is collected by an affinity tag. In other aspects, the quantifying step is achieved using mass spectrometry. In other aspects, the quantification is achieved using another assay such as an ELISA or fluorescence.

DETAILED DESCRIPTION

Figure 1:
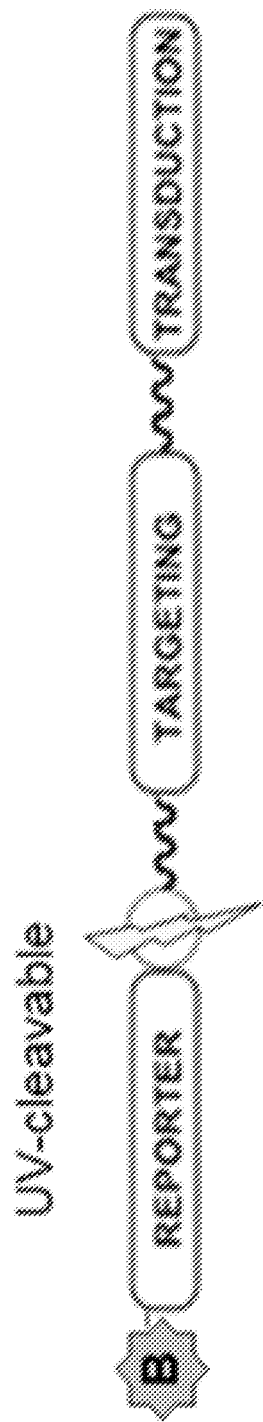
FIG. 1 is a cartoon representation of the biosensor.

Described herein are compositions and methods for measuring tyrosine kinase activity. The compositions comprise synthetic sequences that enable a part or all of the composition to be degradation resistant to proteases. These degradation resistant sequences make up a degradation resistant biosensor, or biosensor as it is referred to throughout the application.

For the purposes of this disclosure, when an amino acid is written in upper case letters it signifies an 'L' amino acid or L-amino acid and when an amino acid is written in lower case letters it signifies a 'D' amino acid or D-amino acid. For the purposes of this disclosure the start of a peptide sequence is associated with the amino (N) terminus, and the end of a sequence is associated with the carboxyl (C) terminus. All sequences are written N terminus to C terminus. One peptide sequence, such as the reporter sequence, targeting sequence, or transduction sequence may be linked or coupled to another sequence. In certain embodiments one peptide sequence is linked to another via a covalent bond.

In certain embodiments, the invention includes a biosensor comprising a peptide comprising a reporter sequence, i.e., an amino acid sequence including a tyrosine residue that can be phosphorylated by a tyrosine kinase. In certain embodiments, the biosensor includes a reporter sequence that can be phosphorylated by Syk, Btk, one or more Src family tyrosine kinases, Jak2, ALK, or Abl. In certain embodiments, the reporter sequence comprises D-amino acids. In certain embodiments the reporter sequence is provided in reverse order. In certain embodiments, the reporter sequence comprises D-amino acids in a reverse order. In certain embodiments, the biosensor includes one or more additional functional elements. In some embodiments, the functional elements include an affinity tag to facilitate capture, isolation or immobilization of the biosensor, or a cleavable linker. In certain embodiments, the biosensor may include an affinity tag, including biotin, such as a biotinylated amino acid, or a poly-His tag. In certain embodiments the biosensor may include a transduction sequence. In certain embodiments the transduction sequence is a cell penetrating peptide. In certain embodiments, the cell penetrating peptide may be Tat. In certain embodiments the transduction sequence comprises D-amino acids. In other embodiments, the transduction sequence is provided in reverse order. In certain embodiments, the transduction sequence may include D-amino acids in reverse order. In certain embodiments, the biosensor may include a cleavable linker, such as a photo-cleavable linker. The photo-cleavable linker may include, for example, a photo-cleavable amino acid analog such as beta(nitrophenyl)alanine. The photo-cleavable linker covalently links two other elements of the biosensor. For example, the reporter sequence may be linked to an affinity tagged peptide sequence and linked through a photo-cleavable linker to a transduction sequence. In other embodiments, the biosensor is designed to include a photo-cleavable linker between the reporter sequence and a targeting sequence. In certain embodiments the affinity tag is linked to the reporter sequence, the reporter sequence is linked to a targeting sequence, and the targeting sequence is linked to the transduction sequence. In other embodiments the biosensor includes an affinity tag which is linked to a reporter sequence, the reporter sequence is linked to a cleavable linker, the cleavable linker is linked to a targeting sequence, and the targeting sequence is linked to a transduction sequence.

In certain embodiments, the biosensor comprises a targeting sequence. The targeting sequence includes a protein interaction domain or a fragment thereof. In certain embodiments the targeting sequence comprises a protein interaction domain selected from the group consisting of 14-3-3 domain, ADF domain, ANK repeat domain, arm domain, BAR domain, BEACH domain, BH1-BH2-BH3-BH4 domain, BIR domain, BRCT domain, Bromo domain, BTB domain, C1 domain, C2 domain, CARD domain, CC domain, CALM domain, CH domain, Chr domain. CUE domain, DD domain, DED domain, DEP domain, DH domain, EFh domain, EH domain, ENTH domain, EVH1 domain, F-box domain, FERM domain, FF domain, FH2 domain, FHA domain, FYVE domain, GAT domain, GEL domain, GLUE domain, GRAM domain, GRIP domain, GYF domain, HEAT domain, hect domain, I Q domain, LIM domain, LRR domain, MBT domain, MH1 domain, MH2 domain, MIU domain, NZF domain, PAS domain, PB1 domain, PDZ domain, PH domain, Polo Box domain, PTB domain, PUF domain, PWWP domain, PX domain, RGS domain, RING domain, SAM domain, SC domain, SH2 domain, SH3 domain, SOCS domain, SPRY domain, START domain, SWIRM domain, TIR domain, TPR domain, TRAF domain, tsnare domain, Tubby domain, TUDOR domain, UBA domain, UEV domain. UIM domain, VHLbeta domain, VHS domain, W domain, and WW domain. In certain embodiments the targeting domain is a protein interaction domain of a kinase. In certain aspects the targeting sequence may include at least one L-amino acid at the C-terminus of the amino acid sequence. In certain embodiments at least one L-amino acid, such as glycine (G) or 'GCG' links the C terminus of the reporter sequence to the N terminus of the targeting sequence. In other aspects, at least one L-amino acid, such as 'G' or 'GCG' links the photo-cleavable linker to the targeting sequence.

In certain embodiments, the biosensor comprises a reporter sequence for Syk, Btk, one or more Src family tyrosine kinases, ALK, Jak2, or Abl.

In certain embodiments, the composition may include a Syk-specific biosensor comprising a reporter sequence selected from the group consisting of dpeeydeed (SEQ ID NO:1), pedpeeydeed (SEQ ID NO:2), npseyddee (SEQ ID NO:3), npseysdee (SEQ ID NO:4), npsdysdee (SEQ ID NO:5), penpseyddee (SEQ ID NO:6), penpseysdee (SEQ ID NO:7), penpsdysdee (SEQ ID NO:8), gpenpseyddeegg (SEQ ID NO:9), ggpenpseysdeegg (SEQ ID NO:10), ggnpspdysdeegg (SEQ ID NO:11), ggpedpeeydeedgg (SEQ ID NO:12), or ggnpsdysdeegg (SEQ ID NO:13). In certain embodiments, the reporter sequence includes an affinity tag. In certain embodiments, the reporter sequence may start with a biotinylated lysine residue ($K_{biotin}$). In other embodiments, the reporter sequence ends with at least one L-amino acid, such as 'G' or 'GCG' for linking to another sequence such as a cleavable linker. In certain embodiments the reporter sequence includes the following generic composition ($K_{biotin}$)-reporter sequence-(L-amino acid).

In certain embodiments, the composition may include a Btk-specific biosensor that includes enelyadle (SEQ ID NO:14), enelygale (SEQ ID NO:15), lqeeyvdle (SEQ ID NO:16), or tqevyvdle (SEQ ID NO:17). In certain embodiments, the reporter sequence includes an affinity tag. In certain embodiments, the reporter sequence may start with a biotinylated lysine residue ($K_{biotin}$). In other embodiments, the reporter sequence ends with at least one L-amino acid, such as 'G' or 'GCG' for linking to another sequence such as a cleavable linker. In certain embodiments the reporter sequence includes the following generic composition ($K_{biotin}$)-reporter sequence-(L-amino acid).

In certain embodiments, the composition may include a Src family-specific biosensor that includes dleeyided (SEQ ID NO:18), evfdyvdge (SEQ ID NO:19), epqeyvdnn (SEQ ID NO:20), dpmdyvdee (SEQ ID NO:21), dpmdyvdae (SEQ ID NO:22), dleeyidld (SEQ ID NO:23), dmmdyvhae (SEQ ID NO:24), dleeyvded (SEQ ID NO: 33), dvdvydded (SEQ ID NO:34), dvdgydeed (SEQ ID NO:35), dvdeydded (SEQ ID NO:36), dideydded (SEQ ID NO:37), dleeyidkd (SEQ ID NO:38), or dvdgydded (SEQ ID NO:39). In certain embodiments, the reporter sequence includes an affinity tag. In certain embodiments, the reporter sequence may start with a biotinylated lysine residue ($K_{biotin}$). In other embodiments, the reporter sequence ends with at least one L-amino acid, such as 'G' or 'GCG' for linking to another sequence such as a cleavable linker. In certain embodiments the reporter sequence includes the following generic composition ($K_{biotin}$)-reporter sequence-(L-amino acid).

In certain embodiments, the composition may include a Jak2-specific biosensor that includes etriyrdpd (SEQ ID NO:25), elklyrdge (SEQ ID NO:26), dlqvyrgde (SEQ ID NO:27), or dlqvyrpkp (SEQ ID NO:28). In certain embodiments, the reporter sequence includes an affinity tag. In certain embodiments, the reporter sequence may start with a biotinylated lysine residue ($K_{biotin}$) In other embodiments, the reporter sequence ends with at least one L-amino acid, such as 'G' or 'GCG' for linking to another sequence such as a cleavable linker. In certain embodiments the reporter sequence includes the following generic composition ($K_{biotin}$)-reporter sequence-(L-amino acid).

In certain embodiments, the composition may include an Abl-specific biosensor that includes fpaqyaved (SEQ ID NO:29), vwfhyrifd (SEQ ID NO: 30), vpiiyfihd (SEQ ID NO:31), vpihyfihd (SEQ ID NO:32), or kkafpaayiae (SEQ ID NO:40). In certain embodiments, the reporter sequence includes an affinity tag. In certain embodiments, the reporter sequence may start with a biotinylated lysine residue ($K_{biotin}$). In other embodiments, the reporter sequence ends with at least one L-amino acid, such as 'G' or 'GCG' for linking to another sequence such as a cleavable linker. I certain embodiments the reporter sequence includes the following generic composition ($K_{biotin}$)-reporter sequence-(L-amino acid).

In certain embodiments, the composition may include an ALK-specific biosensor the includes smryidrdmdf (SEQ ID NO:41), tntyidrdmdf (SEQ ID NO:42), sdryidrdmdf (SEQ ID NO:43), or tnryidrdmdf (SEQ ID NO:44). In other embodiments, the reporter sequence ends with at least one L-amino acid, such as 'G' or 'GCG' for linking to another sequence such as a cleavable linker. I certain embodiments the reporter sequence includes the following generic composition ($K_{biotin}$)-reporter sequence-(L-amino acid).

In certain embodiments the biosensor includes a transduction sequence. In certain embodiments the transduction sequence is a cell penetrating peptide (CPP). Examples of useful CPPs include, but are not limited to, the TAT peptide, and the protein transduction domains of Penetratin (pAntp), Transportan, MPG, MPGdeltaNLS, and pHLIP. Cell penetrating fragments of a CPP can also be used in a delivery system and/or method of the invention. As used herein, the term CPP includes cell penetrating fragments of protein transduction domains. In other aspects, the transduction sequence is a cell penetrating peptide comprising D-amino acids. In other aspects, the transduction sequence is provided in reverse order. In other aspects, the transduction sequence is provided as D-amino acids and in reverse order. In certain embodiments the transduction sequence includes the sequence rrrqrrkkr (SEQ ID NO: 45). In certain embodiments at least one L-amino acid, such as 'G' or 'GCG' is included in the transduction sequence at the start or N terminus. In certain embodiments the generic composition of the biosensor is reporter sequence targeting sequence-(L-amino acid)-transduction sequence.

In certain embodiments, the biosensor includes a cleavable linker. In certain aspects the cleavable linker is a photo-cleavable linker. In certain aspects the cleavable linker is an amino acid beta(nitrophenyl)alanine or βNpa, also known as 3-(2-nitrophenyl)-3-aminopropionic acid. In certain aspects the reporter sequence is linked or coupled to the cleavable linker through at least one L-amino acid, such as 'G' or 'GCG'.

For the purposes of this disclosure (L-amino acid) is a representation of an amino acid sequence comprising at least one L-amino acid. In certain embodiments the biosensor comprises the following sequences linked in the following order; reporter sequence-targeting sequence-transduction sequence. In certain embodiments the biosensor comprises the following sequences linked in the following order; affinity tag-reporter sequence-targeting sequence-transduction sequence. In certain embodiments the biosensor comprises the following sequences linked in the following order; affinity tag-reporter sequence-cleavable linker-targeting sequence-transduction sequence. In certain embodiments the biosensor comprises the following sequences linked in the following order; affinity tag-reporter sequence-(L-amino acid)-cleavable linker-targeting sequence-transduction sequence as shown in FIG. 1. In certain embodiments the biosensor comprises the following sequences linked in the following order; affinity tag-reporter sequence-(L-amino acid)-cleavable linker-targeting sequence-(L-amino acid)-transduction sequence. In certain embodiments the biosensor comprises the following sequences linked in the following order; affinity tag-reporter-sequence-(L-amino acid)-cleavable linker-(L-amino acid)-targeting sequence-(L-amino acid)-transduction sequence. It is to be understood that other combinations of these generic compositions may exist. Examples of a biosensor shown as an amino acid sequence is as follows; kkafpaayiaeGGCGAPTYSPPPPPG-Grrrqrrkkr (SEQ ID NO:46) or $K_{biotin}$kkafpaayiaeG-photo-cleavable linker-GCGAPTYSPPPPPGGrrrqrrkkr (SEQ ID NO:47) where $K_{biotin}$ represents a biotinylated lysine residue.

In other embodiments are provided methods for detecting tyrosine kinase activity. In certain embodiments, the methods allow detection of the activity of Syk, Btk, one or more Src family tyrosine kinases, Jak2, ALK, or Abl by detecting phosphorylation of a reporter sequence of Syk, Btk, a Src family kinase, Jak2, ALK, or Abl. In certain embodiments, the methods allow "multiplexing" of the detection of tyrosine kinase activity, i.e., detecting the activity of two or more tyrosine kinases in a single reaction. In certain embodiments, the assay is conducted in vitro or in whole cells. In certain embodiments, phosphorylation is detected using ELISA, terbium based time-resolved luminescence, mass spectrometry, MALDI-TOF MS analysis, or multiple reaction monitoring (MRM) on a triple quadrupole mass spectrometer. In certain embodiments, the method is conducted using a reporter sequence or a biosensor comprising the reporter sequence that covalently attach directly or indirectly through an affinity tag to a solid surface, such as a bead, a multi-well plate, or nanoparticle.

In certain embodiments, the methods of the invention may be used to determine the level of tyrosine kinase activity in a biological sample from a mammal, such as a human. In certain embodiments, the methods involve detecting Abl activity in a sample from a person suspected of having or at risk for developing a condition associated with altered tyrosine kinase activity, i.e., tyrosine kinase activity that is increased or decreased relative to the tyrosine kinase activity of a control, e.g., a sample from a person who does not have the condition, or a normal range of tyrosine kinase activity based on the tyrosine kinase activities of samples from a relevant sample of people. In certain embodiments, the sample includes diseased or healthy tissue from any cell lineage. In certain embodiments, the results of the determination may be used in diagnosis or prognosis, or in determining a course of treatment.

In certain embodiments, the methods involve determining the level of Syk activity in a person. In certain embodiments, the person has acute myeloid leukemia (AML). In certain embodiments, the method may involve recommending treatment or treating a person with AML having an increased level of Syk activity relative to a control with a Syk inhibitor. In certain embodiments, the method involves determining the level of Syk activity in a person with chronic lymphocytic leukemia cells (B-CLL). In certain embodiments, the method may involve recommending treatment or treating a person with B-CLL having an increased level of Syk activity relative to a control with a Syk inhibitor. In certain embodiments in which the person has a disorder associated with increased Syk activity, treatment may include administering to the person an effective amount of a Syk inhibitor, such as an siRNA or small molecule Syk inhibitor, some of which are known in the art. In certain embodiments, the method may involve recommending treatment or treating a person with peripheral T-cell lymphomas (PTCLs) In certain embodiments in which the person has a disorder associated with increased Syk activity, treatment may include administering to the person an effective amount of a Syk inhibitor, such as an siRNA or small molecule Syk inhibitor, some of which are known in the art.

In certain embodiments, the methods involve determining the level of Syk activity in a sample from a person with breast cancer. In certain embodiments, the method involves recommending treatment or treating a person with breast cancer cells having reduced expression of Syk, the treatment including administering an effective amount of a Syk agonist, a Syk kinase, or a genetic construct expressing Syk kinase.

In certain embodiments, the methods can be used to determine whether a person with a cancer is likely to benefit from a particular treatment. For example, in certain embodiments, the methods of the invention can be used to detect tyrosine kinase activity in whole cells obtained from the person in the presence and absence of an inhibitor of the tyrosine kinase. In certain embodiments, the methods employ an Abl biosensor to measure phosphorylation of in whole cells from a person with chronic myelogenous leukemia (CML) to assess whether the cells are sensitive or resistant to treatment with imatinib. In certain embodiments, phosphorylation levels of cells treated or not treated with imatinib in vitro are compared, with the absence of a sufficient decrease in phosphorylation of the reporter sequence from imatinib treated cells suggesting that the cancer may not respond to treatment with the inhibitor. In other embodiments, samples are taken from the person with CML at different times to monitor effectiveness as measured by a sustained decrease in phosphorylation of the Abl biosensor following treatment with imatinib. In certain embodiments, the methods are performed using MRM on a triple quadrupole mass spectrometer using relatively few cells, e.g., from 10,000 to 50,000 cells, making testing of clinical samples feasible.

In other embodiments, the methods of the invention can be used to screen for molecules capable of altering tyrosine kinase activity, including molecules that reduce or increase tyrosine kinase activity. In certain embodiments are provided methods for screening for inhibitors of Syk, Btk, one or more Src family tyrosine kinases, Jak2, ALK, or Abl. In certain embodiments, the assays are conducted in a high throughput format. In certain embodiments, the methods employ whole cells that are contacted with the biosensor in the presence and absence of the test molecule to assess whether the agent inhibits intracellular phosphorylation of the reporter sequence.

In certain embodiments are provided kits comprising reporter sequences, for example, reporter sequences immobilized on a solid surface, or comprised within a biosensor. In certain embodiments, the kits may be used to perform the methods of the invention. In certain embodiments, the kits may contain additional components, including, for example, suitable buffers, a kinase such as Syk or Abl, and a phosphorylation detection reagent.

Peptide Synthesis and Purification: Amino acids and other peptide synthesis reagents were purchased through Peptides International (Louisville, Ky., USA). The photo-cleavable linker residue (3-(2-nitrobenzyl)-3-aminopropionic acid was obtained from Lancaster Synthesis and F-moc protection of the residue was performed. The F-moc-L-Lysine(biotinyl)-OH was purchased from Akaal Organics (Long Beach, Calif., USA). Peptide synthesis was performed at a 50 umol scale on CLEAR-Amide resin (mixed with glass beads to prevent clumping of resin) using solid phase F-moc chemistry (F-moc protected amino acid monomer final concentration of 100 mM) on a Prelude Parallel Peptide Synthesizer (Protein Technologies, Tucson, Ariz., USA). Synthesis protocol as follows: coupling 10 min; final 6 residue coupling 30 min; deprotection 2×2 min with a coupling reagent final concentration of 95 mM/200 mM HCTU/NMM (2-(6-chloro-1H-benzotriazole-1yl)-1,1,3,3-tetramethyluronium hexafluorophosphate/N-methylmorpholine. High-performance liquid chromatography (HPLC)/MS (Accela/LTQ, Thermo Finnigan) and MALDI TOF/TOF (Voyager 4800, Applied Biosystems, Foster City, Calif., USA) were used to analyze the peptides. Purification of the peptides was performed using a C18 reverse-phase column on an Agilent Technologies 1200 Series Preparative HPLC system (Santa Clara, Calif., USA). Peptides were labeled with FITC fluorophore (Life Technologies) by maleimide reaction using the manufacturer's protocol.

In Vitro Abl Kinase Assay: The in vitro kinase assays were performed in triplicate in Dulbecco's Phosphate Buffered Saline without Calcium, Magnesium, or Phenol red in water bath maintained at 37° C. The total volume of the assay was 200 uL, and contained 1 mM ATP, 10 mM $MgCl_2$, 5-25 uM of the biosensor, and 6 nM of Arg or Lyn Kinase final concentrations. Initiation of the assay was the addition of 1 uL of Arg Kinase to the reaction mix and heated at 37° C. Aliquots of 20 uL were collected at intervals described over a total run time of up to 60 minutes. Each aliquot was quenched with 20 uL of 0.5 M EDTA, each aliquot was treated with UV light for 20 minutes using a CL-1000 Ultraviolet Crosslinker (UVP, Upland, Calif., USA) to cleave the photo-cleavable linker and free the reporter sequence from the rest of the biosensor.

Cell Culture: K562 cells were grown in Iscove's modified Dulbecco media, IMDM, containing 10% FBS, 1% Penicillin and Streptomycin at 37° C. in an environment of 5% $CO_2$.

K562 cell kinase assay: In cell assays were performed in replicates of 10. K562 cells were incubated with 10 nM nilotinib or 0.1% DMSO for 4 hours prior to the Abl biosensor treatment. 1 mL samples of K562 cells ($1 \times 10^6$ cells/mL) were treated with 25 uM the Abl biosensor for 60 minutes. The incubation was ended by washing the cells twice with sterile PBS (pH=7.0) and lysing the cells in a phosphosafe extraction buffer (Novagen) containing 50 mM EDTA, 50 mM EGTA and Complete protease inhibitor cocktail (Roche). Protein concentrations were determined by Pierce 660 nm Protein Assay.

Biosensor Enrichment: K562 cells were incubated in lysis buffer for 20 minutes. Samples were spun down in 2500×g for 5 minutes at 4° C. Lysate was transferred to new Eppendorf tubes and treated with UV light (CL-1000 Ultraviolet Crosslinker (UVP, Upland, Calif., USA)) for 20 minutes to cleave the photo-cleavable linker. Photocleaved lysate samples were incubated with streptavidin coated agarose beads (Pierce) in 96 well polypropylene filter plate (PALL, Ann Arbor, Mich.) for 20 minutes at room temperature. Following incubation, the plate was spun down at 250×g for 30 seconds over a 96 well collection plate. The wells were washed 4 times with 200 uL of PBS and 2 times with MilliQ water, and spun down for 30 seconds at 250×g after each addition. Beads were resuspended in 15 μL of (75%/25%/0.1%:acetonitrile/water/TFA) elution buffer and shaken for 15 minutes at 600 rpm. Biosensor samples were spotted at 0.5 μL on a MALDI plate with 0.5 μL of matrix (10 mg/mL α-cyano-4-cinnamic acid and 10 mg/mL ammonium hydrogen phosphate, dissolved in 75%/25%/0.1% acetonitrile/water/TFA). Mass analysis was performed using an Applied Biosystems Voyager 4800 MALDI-TOF/TOF using linear positive mode.

On-bead Trypsin Digestion of streptavidin molecules: Following enrichment of the reporter sequence on the streptavidin coated agarose beads, each well of filter plate was incubated with 5 mM DTT in water for about 30 minutes at 37° C. After the DTT incubation, Iodoacetamide (final concentration of 25 mM) was added and incubated in the dark for about 20 minutes. 250 ng of mass spectrometry grade Trypsin (Pierce) was added to each well and allowed to incubate overnight at about 37° C. Following overnight incubation, the plate was spun down at about 250×g for about 30 seconds. An aliquot of about 60 uL of 80%/20%/0.1% acetonitrile/water/formic acid were added to each well and incubated at room temperature for about 20 minutes, followed by an additional spin down at about 250×g for about 30 seconds. Digested peptides were enriched and purified using C18 nutips (Glygen Corp.)

LC-MS/MS Analysis: Peptides were separated by an Accela 1100 High performance LC and analyzed using a Thermo Finnigan Linear Trap Quadrupole (Thermo Finnigan). Separation was carried out using a Zorbax C18 column, flow rate of 500 μL/min, using a linear gradient of increasing acetonitrile. The column was equilibrated at 95% water/5% acetonitrile/0.1% Formic acid for the first two minutes. Acetonitrile was increased from 5-63% over the 2-23.5 min. elution time. Blank injections were run between samples to eliminate any carry over between samples.

Flow Cytometry: K562 cells (about 1×10⁶ cells/mL) were incubated for 30 minutes with FITC labeled biosensors at various concentrations, 1-50 μM. Cells were centrifuged at about 2500 rpm for about 5 minutes at 4° C. Media was aspirated and cells were washed 3 times with fresh media. A FC500 flow cytometer (Beckman Coulter) was used to analyze 50 μL aliquots of suspended cells.

In order to generate a more biostable biosensor, the amino terminal module of our previously reported peptide (the Abl reporter sequence EAIYAAPFAKKK$_{biotin}$G) (SEQ ID NO: 48) was modified to its reverse order, composed of D-amino acids, to form an Abl biosensor reporter sequence kkafpaayiaeG (SEQ ID NO: 40) and added an affinity tag and L-amino acid on the C-terminus; K$_{biotin}$kkafpaayiaeG (SEQ ID NO: 49). At the carboxyl end of the biosensor, a reverse order TAT peptide sequence was included. The central Abl SH3 domain binding module APTYSPPPPPGG (SEQ ID NO: 50) was included as a targeting sequence. This Abl kinase binding ligand, was shown to bind the SH3 domain of Abl kinase. The SH3 binding module which contains five proline residues was maintained in the L-stereochemistry in order to avoid previously described issues with opposite handedness for D-proline helices, which would dramatically change the side-chain topology and thus may disrupt interaction with the SH3 domain of the protein. A control peptide was also generated containing only the Abl reporter sequence coupled to the transduction sequence (SEQ ID NO: 53), as were the native L-stereochemistry versions of the biosensor with (SEQ ID NO: 52) and without the SH3 targeting sequence (SEQ ID NO:54). The peptide sequences described in the following examples are given in Table 1.

TABLE 1

| SEQ Name | Sequence |
|---|---|
| 47 | K$_{biotin}$kkafpaayiaeG-photo-cleavable linker-GCGAPTYSPPPPPGGrrrqrrkkr |
| 52 | EAIYAAFAKKG-K$_{biotin}$-photo-cleavable linker-GCGAPTYSPPPPPGGRKKRRQRRR |
| 53 | K$_{biotin}$kkafpaayiaeG-photo-cleavable linker-GCGGrrrqrrkkr |
| 54 | EAIYAAPFAKKG-Kbiotin-photo-cleavable linker-GCGGRKKRRQRRR |

Figure 2:
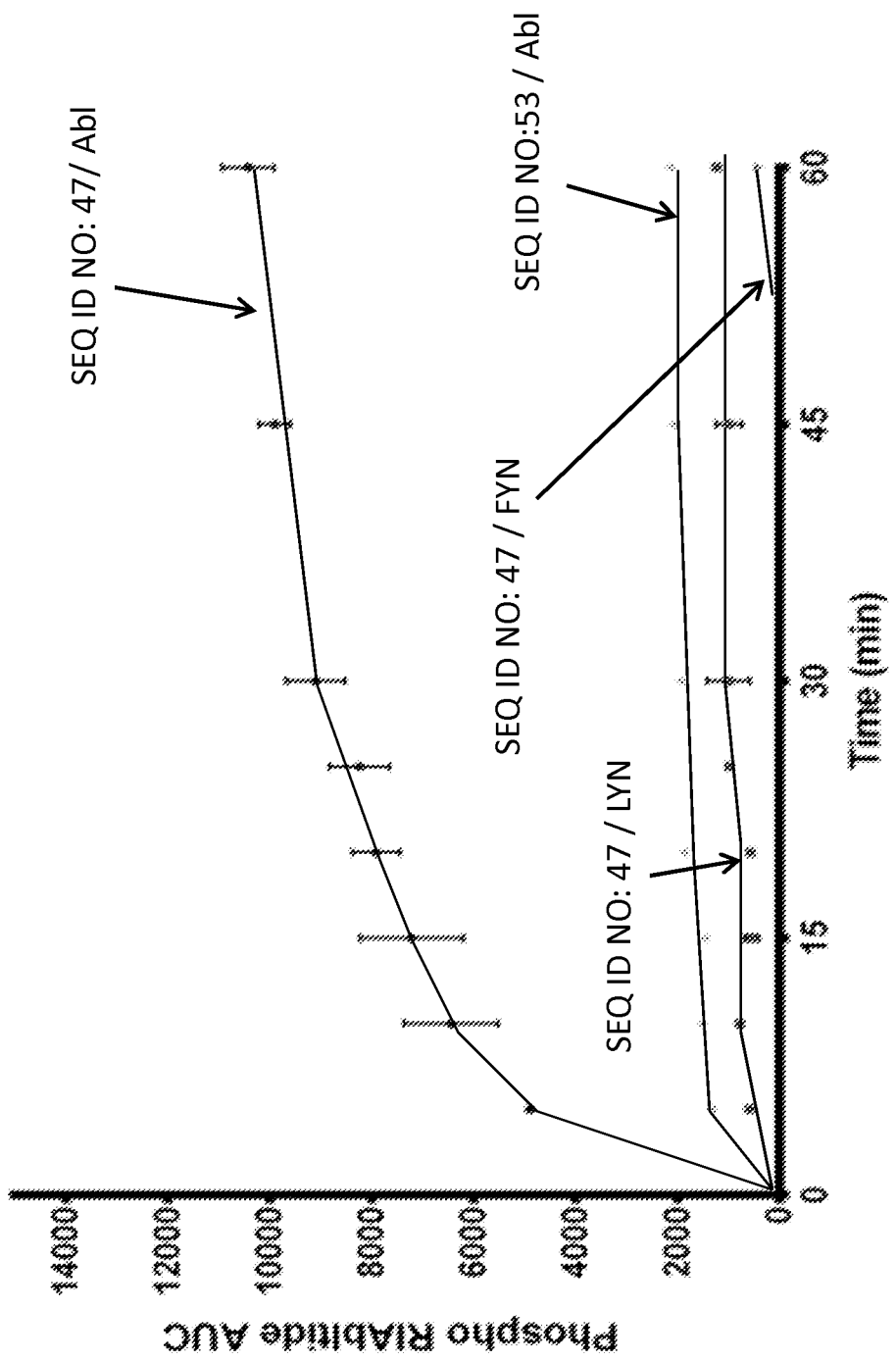
FIG. 2 is a graph depicting the phosphorylation of an Abl reporter sequence coupled to a targeting domain or not coupled to a targeting domain, and showing specificity for Abl Kinase over other kinases.
Figure 3:
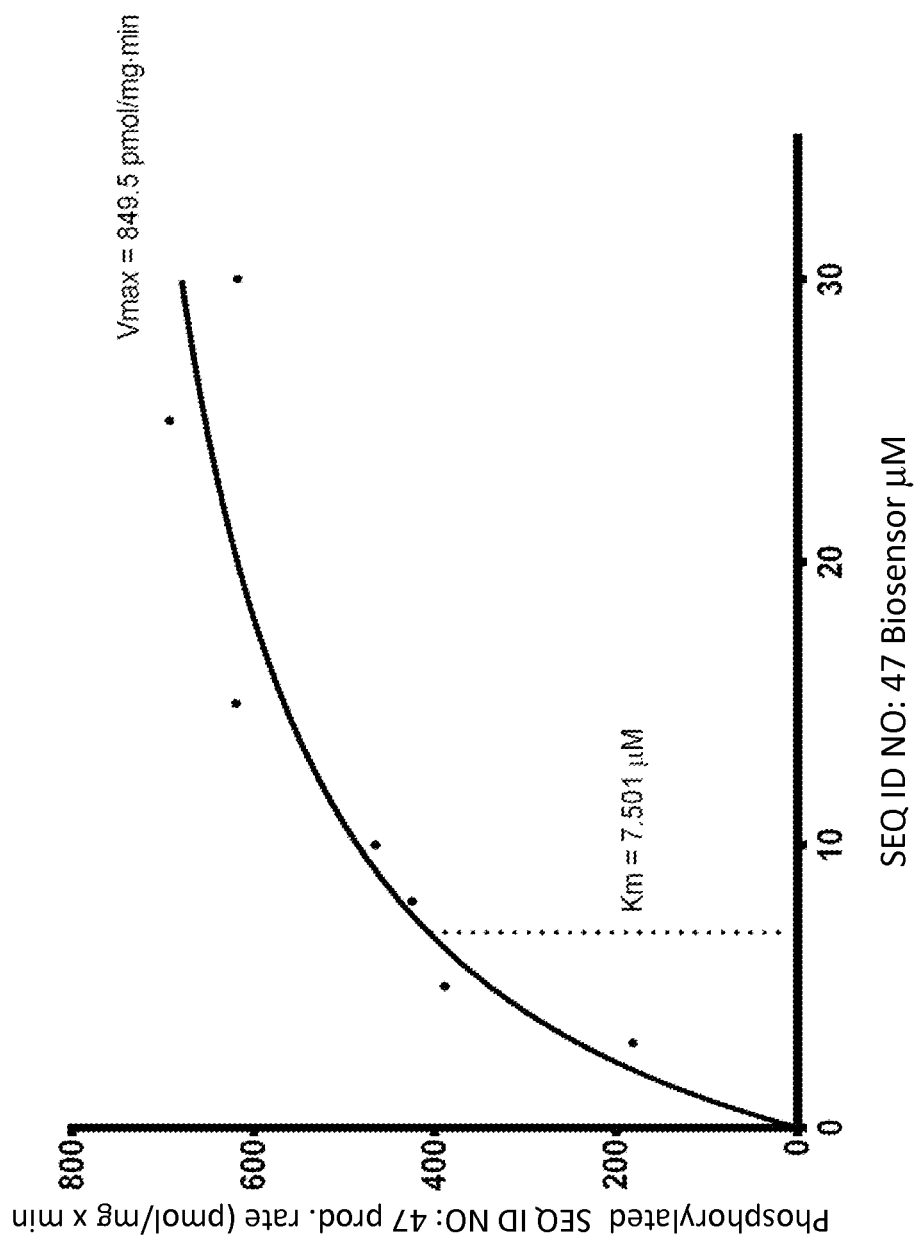
FIG. 3 is a Michaelis Menten graph used to determine the kinetic constants, Vmax and Km, of the biosensor incubated with Abl kinase.

Referring now to FIG. 2, to evaluate the importance of the SH3 targeting sequence, we performed in vitro kinase assays comparing the peptides using the Abl kinase. Phosphorylation was detected using mass spectrometry. We found SEQ ID NO: 53 was not appreciably phosphorylated; however, when the SH3 targeting sequence was present in the full-length, SEQ ID NO:47 was phosphorylated with reasonable efficiency. Further in vitro work determined the michaelismenton constants of the biosensor SEQ ID NO:47 to be the following: $K_m$=7.5 μm and $V_{max}$=849.5 pmol/mg·min as shown in FIG. 3.

In order to assess the selectivity of the biosensor SEQ ID NO: 47, we tested against Lyn and Fyn kinases using the in vitro kinase assay. Lyn kinase is a member of the Src family of kinases and is reported to be upregulated in some drug resistant forms of CML. Lyn kinase did not phosphorylate the biosensor, suggesting that the substrate is selective for Abl over Lyn or Fyn kinases as shown in FIG. 2. This indicates that both the reporter sequence SEQ ID NO:53 and SEQ ID NO:47 are relatively selective toward the Abl family of kinases.

Figure 4:
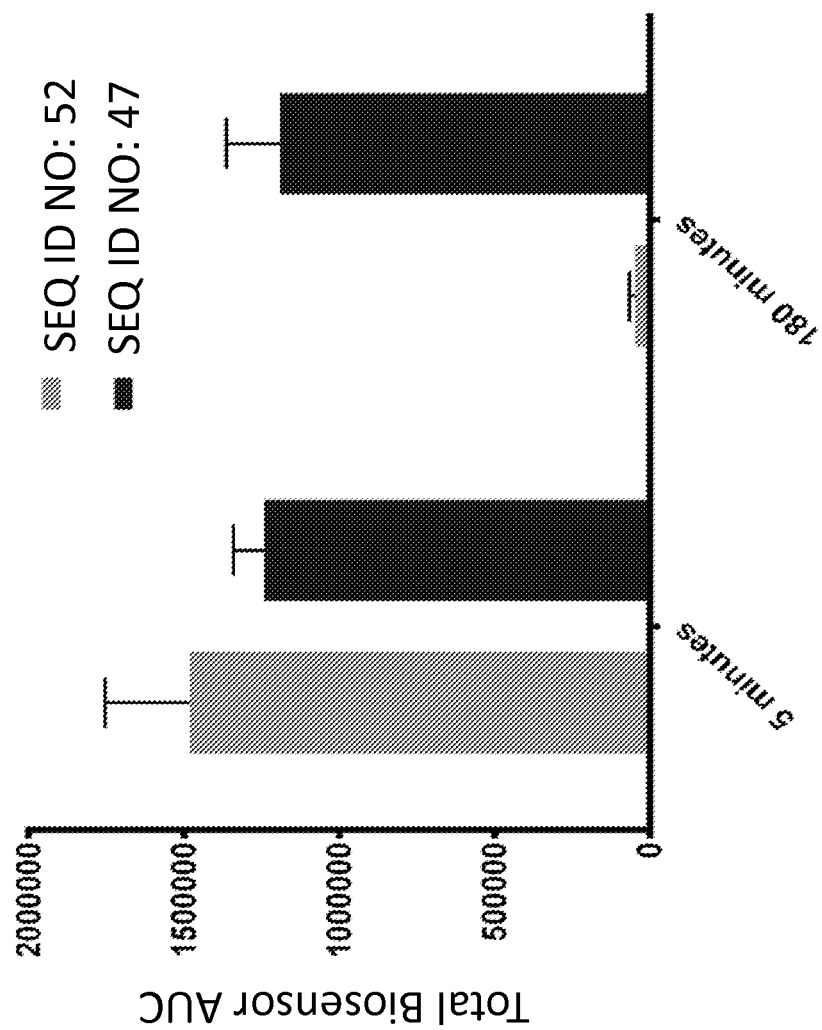
FIG. 4 is a graph depicting the end point degradation of the RI-Abl biosensor in comparison to the original Abl biosensor design.

Next we used the CML model cell line K562, which overexpress Bcr-Abl kinase, to evaluate uptake, stability, and intracellular phosphorylation of the biosensor SEQ ID NO: 47. To characterize the resistance to cellular peptidase and protease degradation in vitro, we incubated the control biosensor SEQ ID NO:52 and the biosensor SEQ ID NO:47 with 30 ug of K562 cell lysate (prepared without protease inhibitor to contain active proteases) for 180 min and measured the relative amount of total peptide detected by mass spectrometry. The results shown in FIG. 4 demonstrated that the biosensor SEQ ID NO:47 is resistant to degradation by endogenous proteases.

Figure 5:
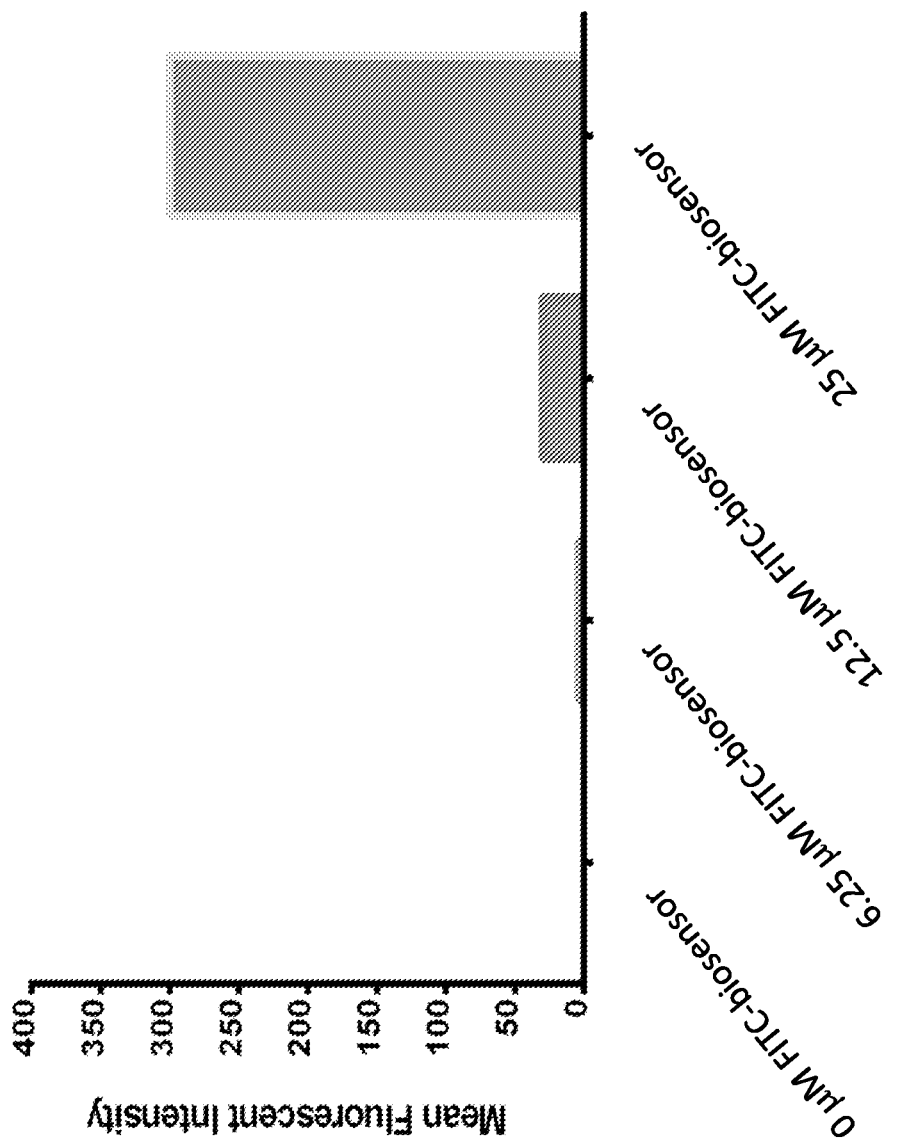
FIG. 5 is a graph depicting a concentration dependent increase in mean fluorescent intensity of a FITC-biosensor incubated with K562 cells of 1 hour.

Flow cytometry was used to verify the uptake of the biosensor SEQ ID NO:47 by K562 cells. We conjugated a FITC fluorophore to the cysteine residue of the biosensor by maleimide reaction. We examined the uptake of the biosensor by shift in FITC labeled cell detection both over time and with increasing concentration of the biosensor, and confirmed the uptake of the biosensor by K562 cells as shown in FIG. 5. Uptake of the biosensor was similar to the uptake of SEQ ID NO: 52, the original Abl biosensor comprising L-amino acid.

Figure 6:
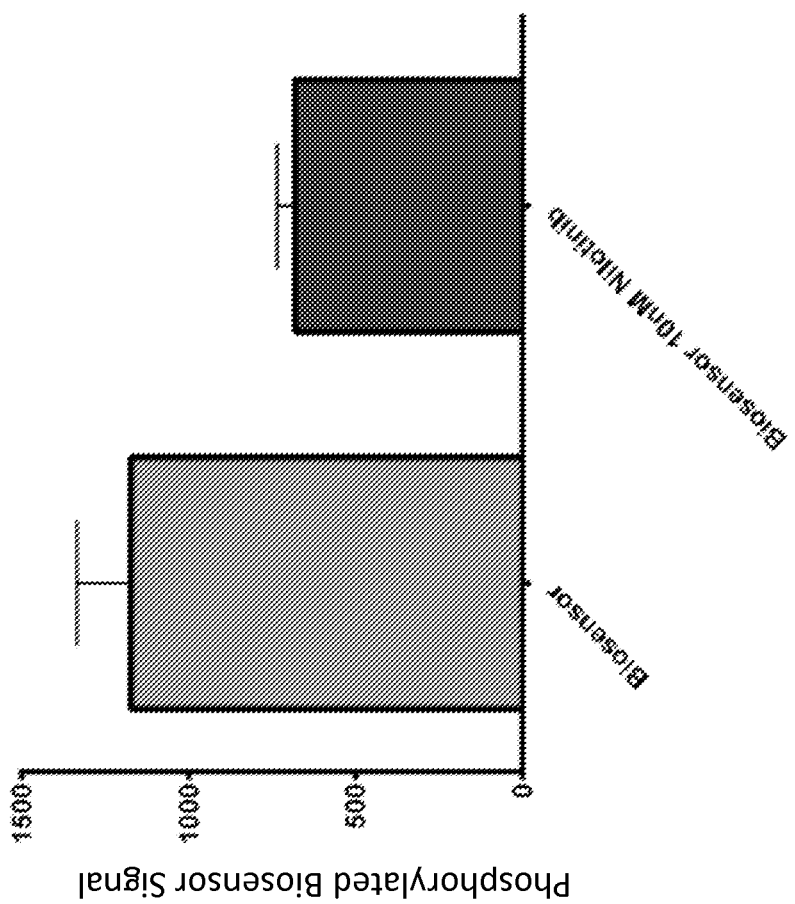
FIG. 6 is a graph quantifying the phosphorylation activity of the biosensor in the presence and absence of nilotinib.
Figure 7:
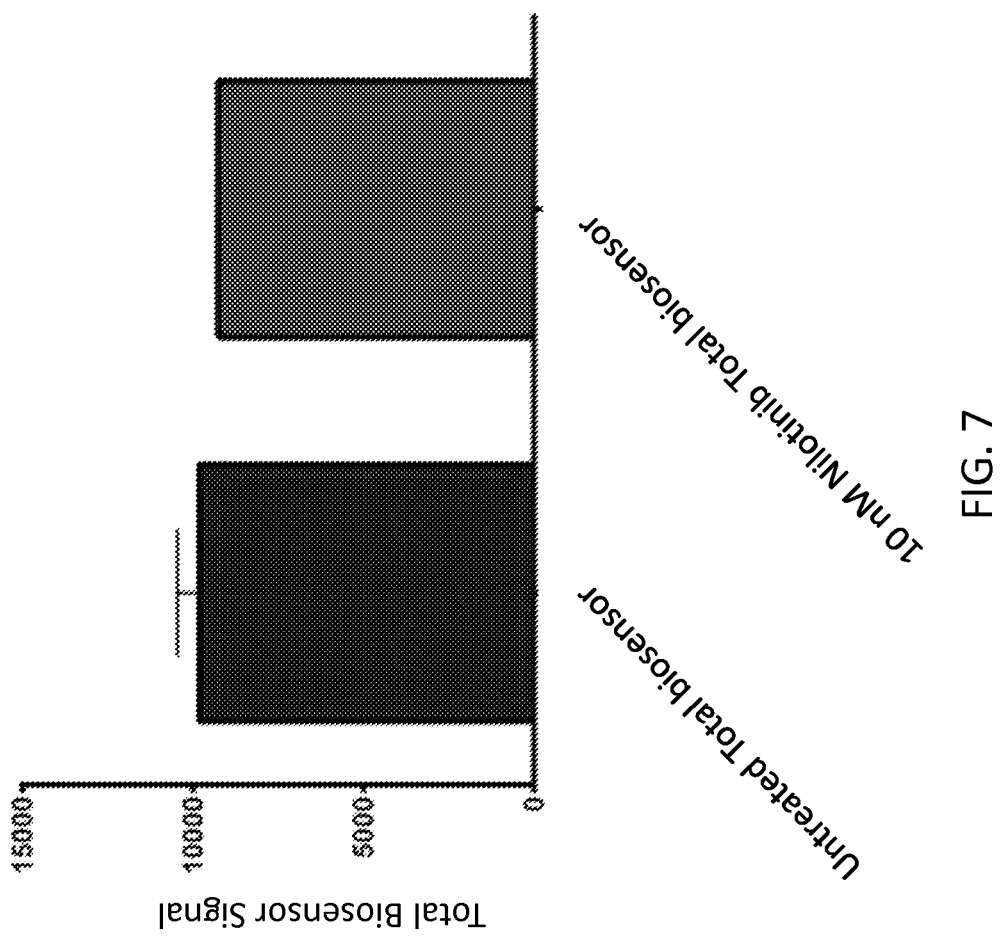
FIG. 7 is a graph quantifying the total amount of biosensor used in the quantification of phosphorylation in FIG. 6.
Figure 8:
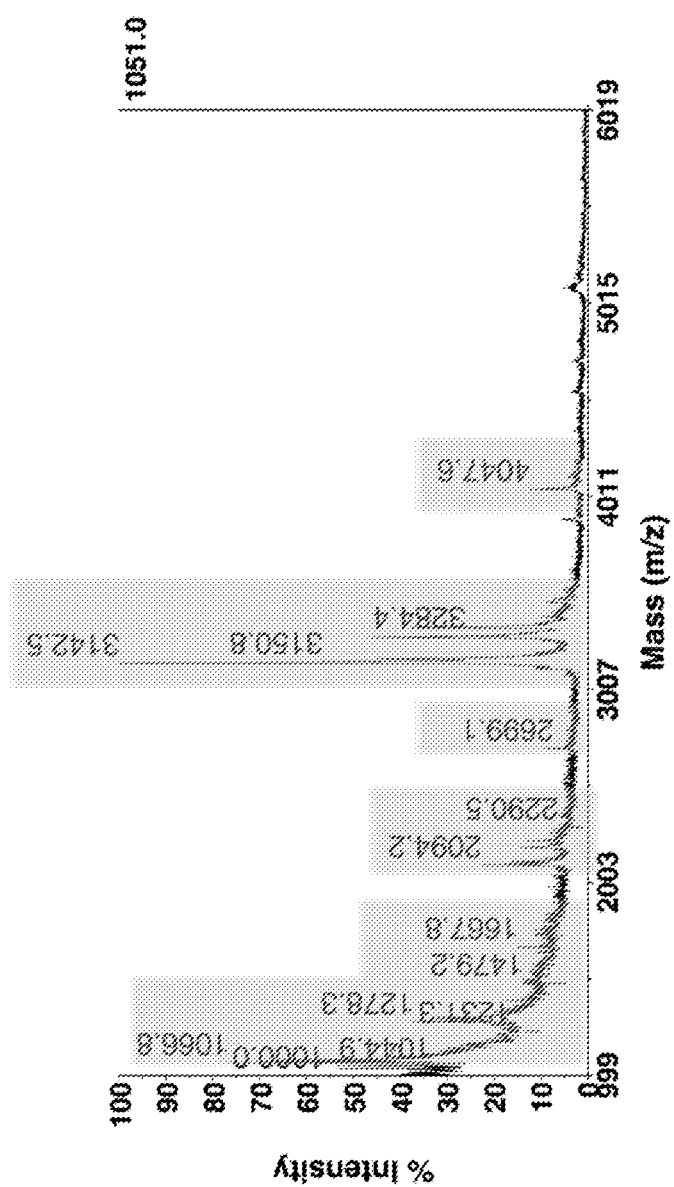
FIG. 8 is a mass spectrum showing the background from K562 cells not treated with a biosensor.
Figure 9:
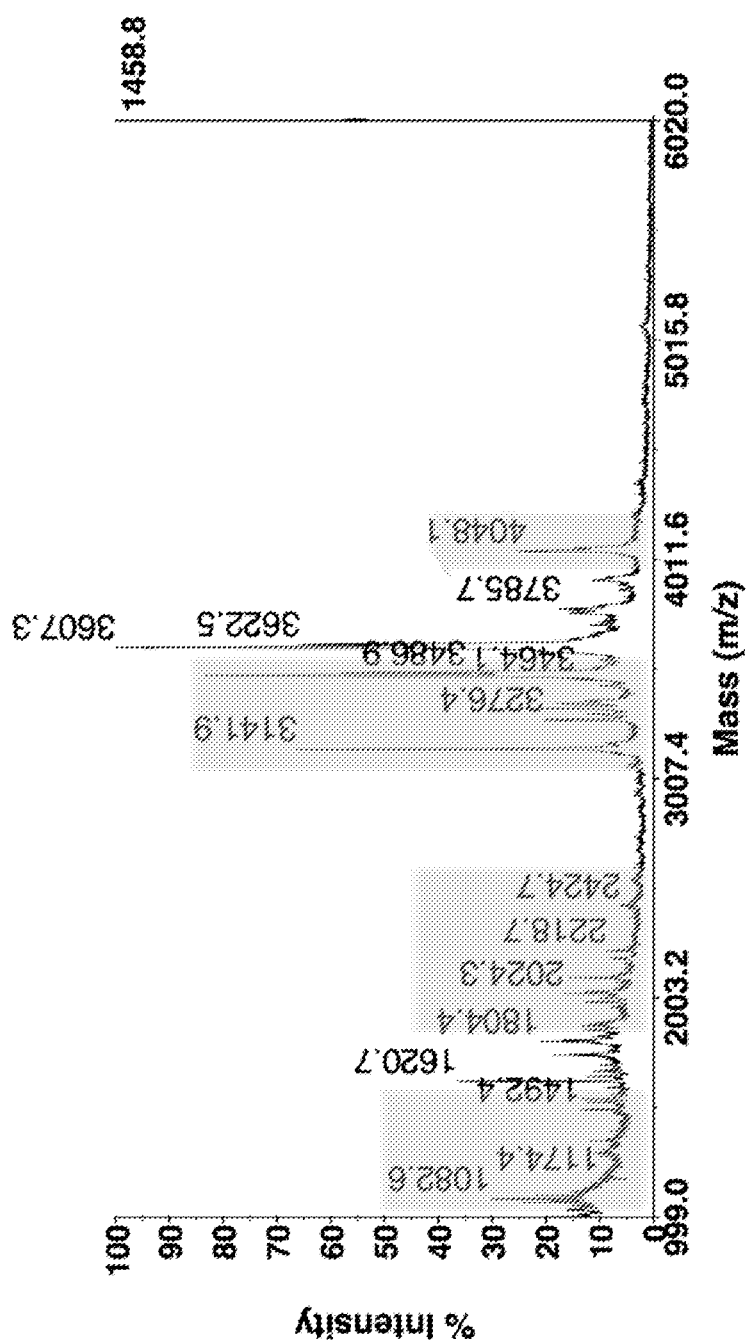
FIG. 9 is a mass spectrum showing degradation of a non-degradation resistant Abl biosensor peptide, where a peak at 4753.30 m/z should appear if not degraded.
Figure 10:
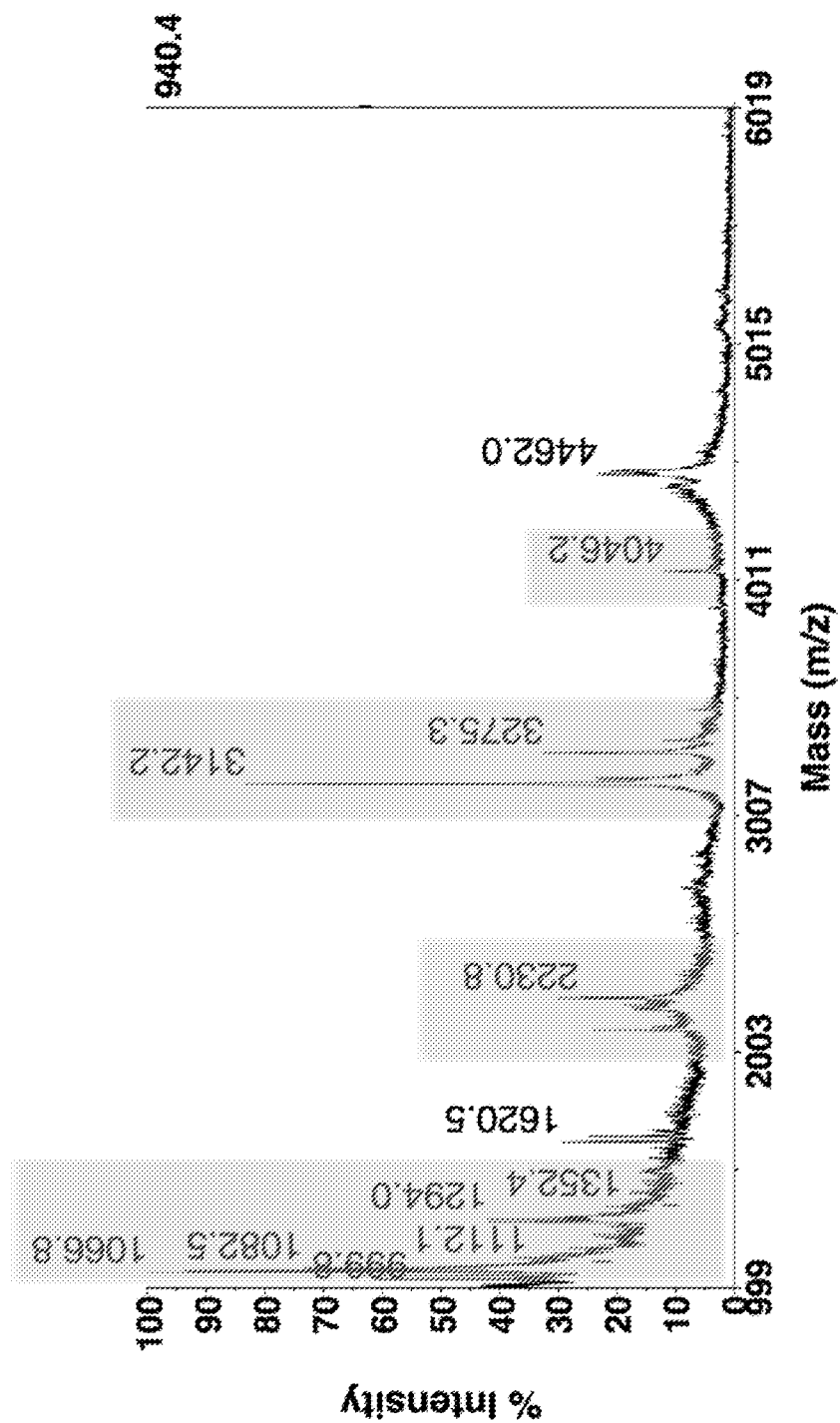
FIG. 10 is a mass spectrum showing the degradation resistant biosensor, or biosensor, signal at 4462.50 m/z after exposure to K562 cells.
Figure 11:
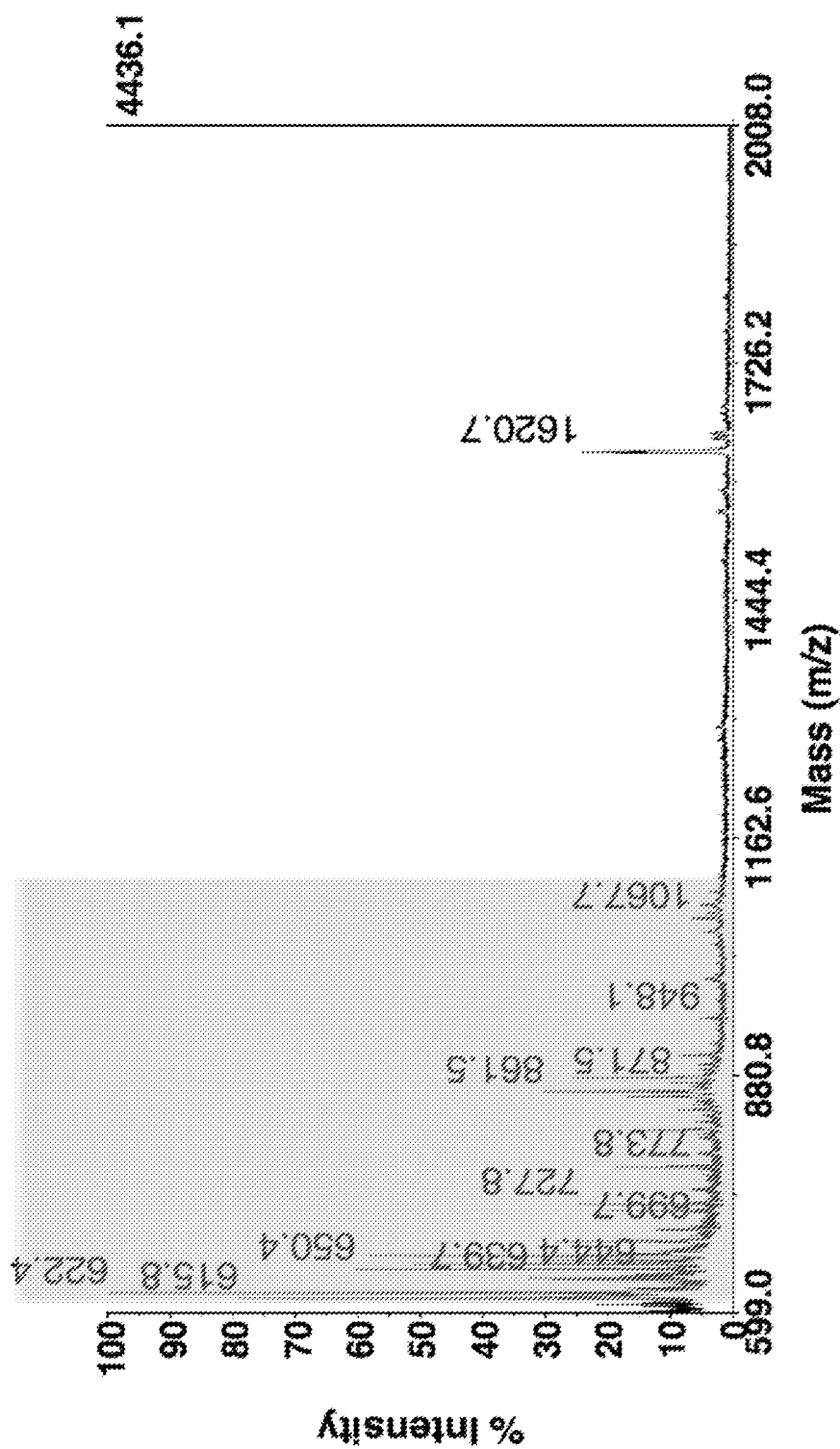
FIG. 11 is a mass spectrum showing the signal of the reporter sequence in the K562 cell lysate, which was cleaved by the photocleavable linker after 20 minutes exposure to UV, with the signal appearing at 1620.90 m/z.
Figure 12:
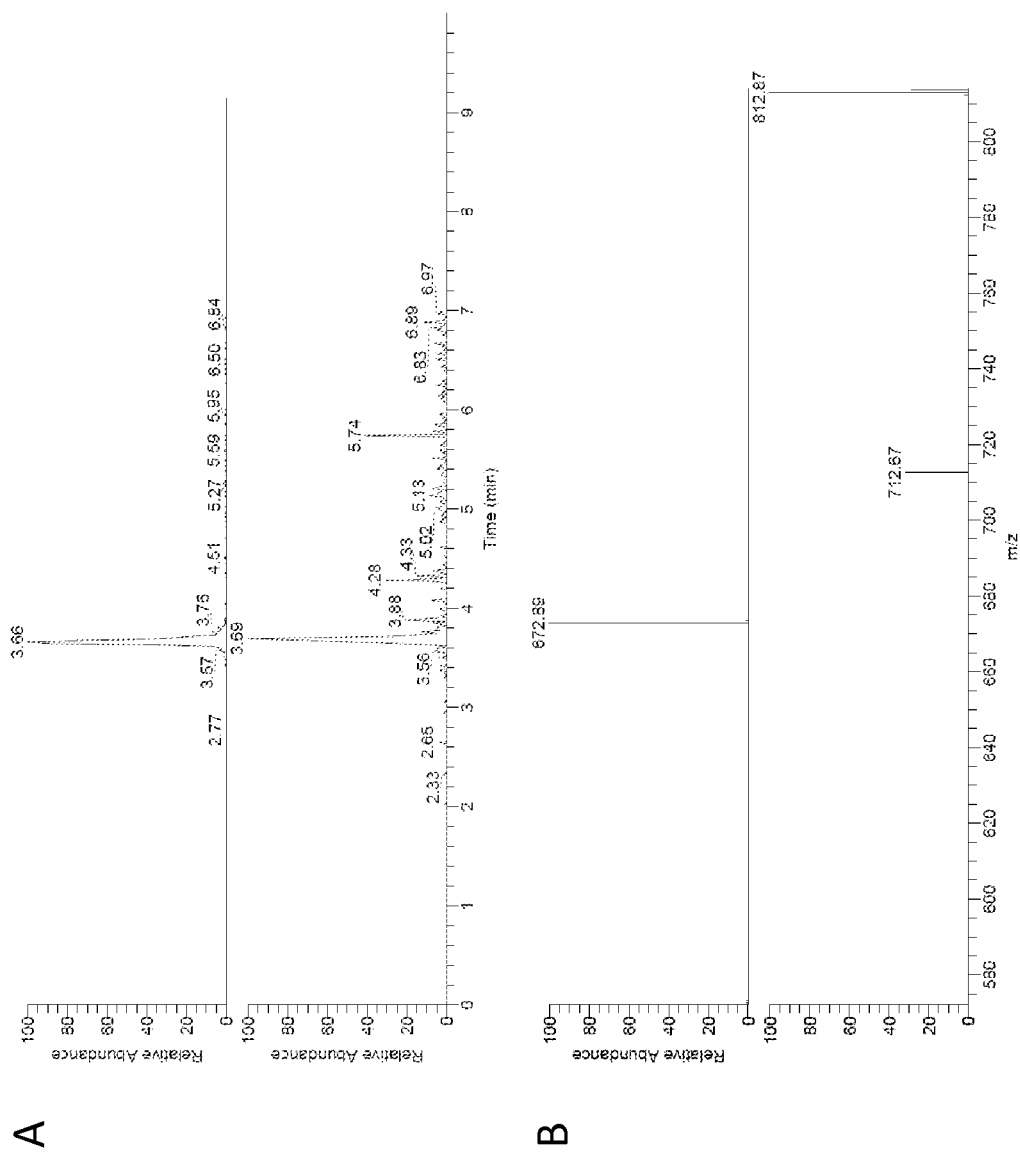
FIG. 12A-B are graphs with FIG. 12A showing an LC elution profile and FIG. 12B showing an MRM chromatogram and mass spectra of the unphosphorylated (parent ion 810.10) and phosphorylated (parent ion 850.10) SEQ ID NO:47 reporter module enriched from K562 cell lysate.
Figure 13:
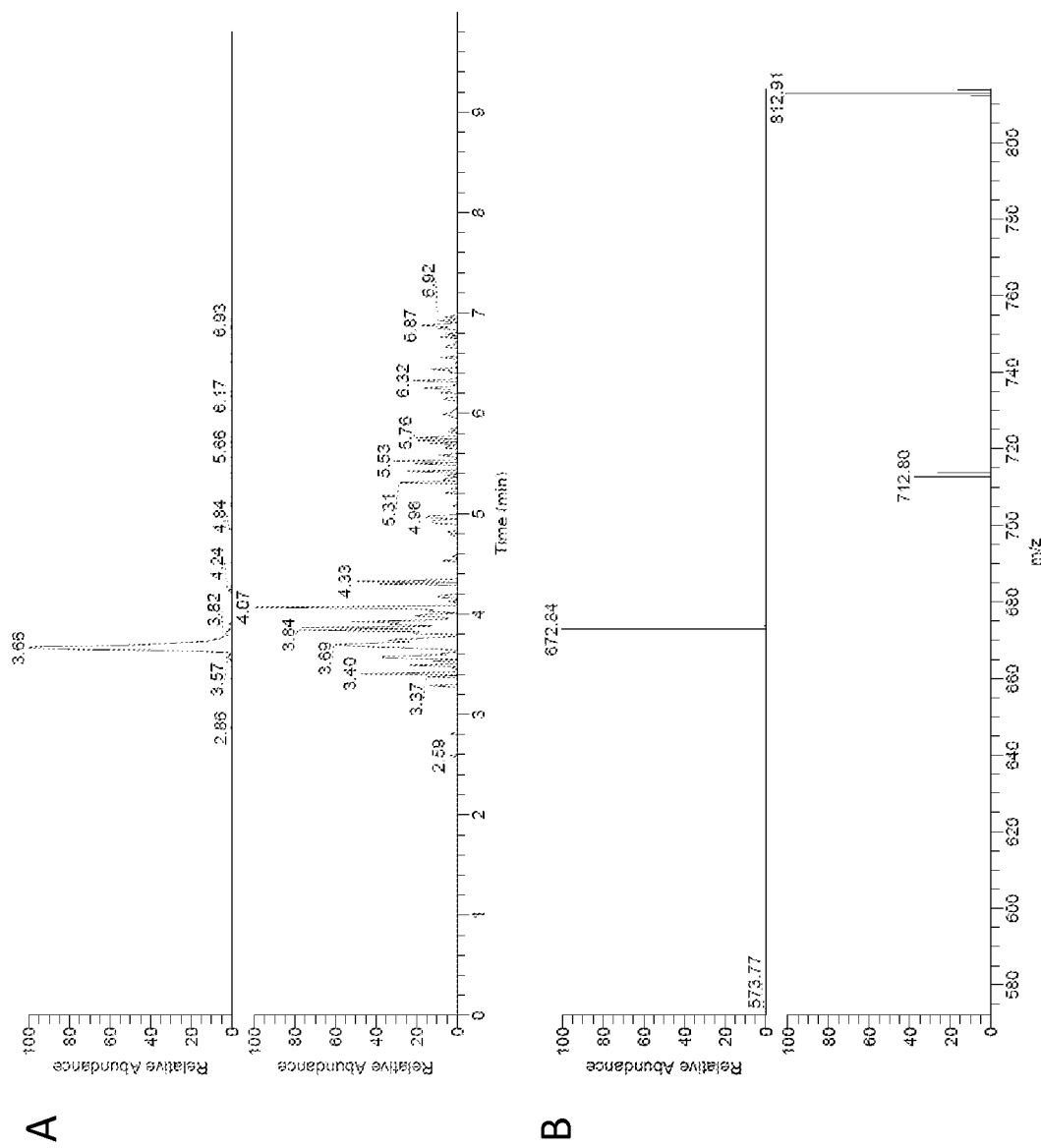
FIG. 13A-B are graphs with FIG. 13A showing an LC elution profile and FIG. 13B showing an MRM chromatogram and mass spectra of the unphosphorylated (parent ion 810.10) and phosphorylated (parent ion 850.10) SEQ ID NO: 47 reporter module enriched from K562 cell lysate treated with nilotinib.

To measure intracellular phosphorylation the original L-form, SEQ ID NO: 52 and the biosensor SEQ ID NO: 47 were incubated with K562 cells for 60 minutes. 10 nM nilotinib was used as a negative control, 4 h pre-incubation with cells prior to biosensor addition. nilotinib is a selective inhibitor of the Abl family, with reported $IC_{50}$ values of roughly 10-50 nM (Abl) and >10 μm (Src). Phosphorylation of the biosensor SEQ ID NO: 47 was observed and inhibited by nilotinib as shown in FIG. 6 and total biosensor signal shown in FIG. 7.

Human K562 chronic myelogenous leukemia (CML) cells were exposed to either the control biosensor SEQ ID NO: 52 or the biosensor SEQ ID NO: 47 for 5 minutes as shown in FIGS. 8-13. The cells were then lysed and the lysates incubated with streptavidin-coated magnetic beads to capture the biotinylated peptides and any degradation products formed through peptidase/protease processing. While the control biosensor was almost completely degraded into smaller components, the biosensor was essentially intact, with no detectable degradation products present. When lysates were exposed to UV light to achieve photocleavage of the cleavable linker and subsequently incubated with streptavidin-coated beads to capture the cleaved reporter sequence, only the biosensor reporter sequence produced any detectable signal.

The invention claimed is:

1. A biosensor comprising:
a reporter sequence configured to resist degradation from proteases, wherein the reporter sequence is kkafpaayiae (SEQ ID NO:40);
a targeting sequence coupled to the reporter sequence and configured to bind to a protein interaction domain of a kinase; and
a transduction sequence coupled to the targeting sequence and configured to resist degradation from proteases, wherein said transduction sequence comprises an amino acid sequence of D-amino acids.

2. The biosensor of claim 1, wherein the biosensor further includes a cleavable linker between the reporter sequence and the targeting sequence.

3. The biosensor of claim 2, wherein the cleavable linker is a UV-photocleavable linker.

4. The biosensor of claim 1, wherein the biosensor further includes a biotinylated lysine residue within the reporter sequence.

5. The biosensor of claim 1, wherein the reporter sequence is an amino acid sequence comprising D-amino acids.

6. The biosensor of claim 5, wherein the reporter sequence further includes a reversed amino acid sequence.

7. The biosensor of claim 1, wherein the transduction sequence further includes a reversed D-amino acid sequence.

8. The biosensor of claim 7, wherein the transduction sequence is a cell penetrating peptide sequence comprising D-amino acids in reverse order.

9. The biosensor of claim 8, wherein the transduction sequence is rrrqrrkkr (SEQ. ID. NO. 45).

10. The biosensor of claim 1, wherein the transduction sequence is a cell penetrating peptide sequence.

11. The biosensor of claim 1, wherein the transduction sequence is an amino acid sequence comprising D-amino acids.

12. The biosensor of claim 11, wherein the transduction sequence further includes a reversed amino acid sequence.

13. The biosensor of claim 12, wherein the transduction sequence is rrrqrrkkr (SEQ ID NO: 45).

14. A method of quantifying phosphorylation of a kinase comprising:
   providing a sample including at least one cell having a kinase of interest;
   contacting the sample with a biosensor comprising a reporter sequence configured to resist degradation from proteases, a targeting sequence coupled to the reporter sequence and configured to bind to a protein interaction domain of a kinase, and a transduction sequence coupled to the targeting sequence and configured to resist degradation from proteases, wherein the reporter sequence is kkafpaayiae (SEQ ID NO:40), the transduction sequence comprises an amino acid sequence of D-amino acids, and the biosensor includes a cleavable linker coupled between the reporter sequence and the targeting sequence;
   cleaving the cleavable linker on the biosensor; collecting the reporter sequence;
   and quantifying phosphorylation of the sample.

15. The method of claim 14, wherein the quantifying is achieved using mass spectometry.

* * * * *

SEQUENCE LISTING

```
<160> NUMBER OF SEQ ID NOS: 54

<210> SEQ ID NO 1
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(9)
<223> OTHER INFORMATION: All D-amino acids

<400> SEQUENCE: 1

Asp Pro Glu Glu Tyr Asp Glu Glu Asp
1               5

<210> SEQ ID NO 2
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(11)
<223> OTHER INFORMATION: All D-amino acids

<400> SEQUENCE: 2

Pro Glu Asp Pro Glu Glu Tyr Asp Glu Glu Asp
1               5                   10

<210> SEQ ID NO 3
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(9)
<223> OTHER INFORMATION: All D-amino acids

<400> SEQUENCE: 3

Asn Pro Ser Glu Tyr Asp Asp Glu Glu
1               5

<210> SEQ ID NO 4
<211> LENGTH: 9
<212> TYPE: PRT
<213> ORGANISM: Artificial Sequence
```

```
<220> FEATURE:
<223> OTHER INFORMATION: Synthesized
<220> FEATURE:
<221> NAME/KEY: MOD_RES
<222> LOCATION: (1)..(9)
<223> OTHER INFORMATION: All D-amino acids

<400> SEQUENCE: 4

Asn Pro Ser Glu Tyr Ser Asp Glu Glu
1               5

<210> SEQ ID NO 5
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(9)
<223> OTHER INFORMATION: All D-amino acids

<400> SEQUENCE: 5

Asn Pro Ser Asp Tyr Ser Asp Glu Glu
1               5

<210> SEQ ID NO 6
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(11)
<223> OTHER INFORMATION: All D-amino acids

<400> SEQUENCE: 6

Pro Glu Asn Pro Ser Glu Tyr Asp Asp Glu Glu
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(11)
<223> OTHER INFORMATION: All D-amino acids

<400> SEQUENCE: 7

Pro Glu Asn Pro Ser Glu Tyr Ser Asp Glu Glu
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(11)
<223> OTHER INFORMATION: All D-amino acids

<400> SEQUENCE: 8

Pro Glu Asn Pro Ser Asp Tyr Ser Asp Glu Glu
1               5                   10
```

<210> SEQ ID NO 9
<211> LENGTH: 14
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(14)
<223> OTHER INFORMATION: All D-amino acids

<400> SEQUENCE: 9

Gly Pro Glu Asn Pro Ser Glu Tyr Asp Asp Glu Glu Gly Gly
1               5                   10

<210> SEQ ID NO 10
<211> LENGTH: 15
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(15)
<223> OTHER INFORMATION: All D-amino acids

<400> SEQUENCE: 10

Gly Gly Pro Glu Asn Pro Ser Glu Tyr Ser Asp Glu Glu Gly Gly
1               5                   10                  15

<210> SEQ ID NO 11
<211> LENGTH: 14
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(14)
<223> OTHER INFORMATION: All D-amino acids

<400> SEQUENCE: 11

Gly Gly Asn Pro Ser Pro Asp Tyr Ser Asp Glu Glu Gly Gly
1               5                   10

<210> SEQ ID NO 12
<211> LENGTH: 15
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(15)
<223> OTHER INFORMATION: All D-amino acids

<400> SEQUENCE: 12

Gly Gly Pro Glu Asp Pro Glu Glu Tyr Asp Glu Glu Asp Gly Gly
1               5                   10                  15

<210> SEQ ID NO 13
<211> LENGTH: 13
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(13)

<223> OTHER INFORMATION: All D-amino acids

<400> SEQUENCE: 13

Gly Gly Asn Pro Ser Asp Tyr Ser Asp Glu Glu Gly Gly
1               5                   10

<210> SEQ ID NO 14
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(9)
<223> OTHER INFORMATION: All D-amino acids

<400> SEQUENCE: 14

Glu Asn Glu Leu Tyr Ala Asp Leu Glu
1               5

<210> SEQ ID NO 15
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(9)
<223> OTHER INFORMATION: All D-amino acids

<400> SEQUENCE: 15

Glu Asn Glu Leu Tyr Gly Ala Leu Glu
1               5

<210> SEQ ID NO 16
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(9)
<223> OTHER INFORMATION: All D-amino acids

<400> SEQUENCE: 16

Leu Gln Glu Glu Tyr Val Asp Leu Glu
1               5

<210> SEQ ID NO 17
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(9)
<223> OTHER INFORMATION: All D-amino acids

<400> SEQUENCE: 17

Thr Gln Glu Val Tyr Val Asp Leu Glu
1               5

<210> SEQ ID NO 18
<211> LENGTH: 9
<212> TYPE: PRT

```
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(9)
<223> OTHER INFORMATION: All D-amino acids

<400> SEQUENCE: 18

Asp Leu Glu Glu Tyr Ile Asp Glu Asp
1               5

<210> SEQ ID NO 19
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(9)
<223> OTHER INFORMATION: All D-amino acids

<400> SEQUENCE: 19

Glu Val Phe Asp Tyr Val Asp Gly Glu
1               5

<210> SEQ ID NO 20
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(9)
<223> OTHER INFORMATION: All D-amino acids

<400> SEQUENCE: 20

Glu Pro Gln Glu Tyr Val Asp Asn Asn
1               5

<210> SEQ ID NO 21
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(9)
<223> OTHER INFORMATION: All D-amino acids

<400> SEQUENCE: 21

Asp Pro Met Asp Tyr Val Asp Glu Glu
1               5

<210> SEQ ID NO 22
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(9)
<223> OTHER INFORMATION: All D-amino acids

<400> SEQUENCE: 22

Asp Pro Met Asp Tyr Val Asp Ala Glu
```

<210> SEQ ID NO 23
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(9)
<223> OTHER INFORMATION: All D-amino acids

<400> SEQUENCE: 23

Asp Leu Glu Glu Tyr Ile Asp Leu Asp
1               5

<210> SEQ ID NO 24
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(9)
<223> OTHER INFORMATION: All D-amino acids

<400> SEQUENCE: 24

Asp Met Met Asp Tyr Val His Ala Glu
1               5

<210> SEQ ID NO 25
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(9)
<223> OTHER INFORMATION: All D-amino acids

<400> SEQUENCE: 25

Glu Thr Arg Ile Tyr Arg Asp Pro Asp
1               5

<210> SEQ ID NO 26
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(9)
<223> OTHER INFORMATION: All D-amino acids

<400> SEQUENCE: 26

Glu Leu Lys Leu Tyr Arg Asp Gly Glu
1               5

<210> SEQ ID NO 27
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES

```
<222> LOCATION: (1)..(9)
<223> OTHER INFORMATION: All D-amino acids

<400> SEQUENCE: 27

Asp Leu Gln Val Tyr Arg Gly Asp Glu
1               5

<210> SEQ ID NO 28
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(9)
<223> OTHER INFORMATION: All D-amino acids

<400> SEQUENCE: 28

Asp Leu Gln Val Tyr Arg Pro Lys Pro
1               5

<210> SEQ ID NO 29
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(9)
<223> OTHER INFORMATION: All D-amino acids

<400> SEQUENCE: 29

Phe Pro Ala Gln Tyr Ala Val Glu Asp
1               5

<210> SEQ ID NO 30
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(9)
<223> OTHER INFORMATION: All D-amino acids

<400> SEQUENCE: 30

Val Trp Phe His Tyr Arg Ile Phe Asp
1               5

<210> SEQ ID NO 31
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(9)
<223> OTHER INFORMATION: All D-amino acids

<400> SEQUENCE: 31

Val Pro Ile Ile Tyr Phe Ile His Asp
1               5

<210> SEQ ID NO 32
<211> LENGTH: 9
```

```
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(9)
<223> OTHER INFORMATION: All D-amino acids

<400> SEQUENCE: 32

Val Pro Ile His Tyr Phe Ile His Asp
1               5

<210> SEQ ID NO 33
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(9)
<223> OTHER INFORMATION: All D-amino acids

<400> SEQUENCE: 33

Asp Leu Glu Glu Tyr Val Asp Glu Asp
1               5

<210> SEQ ID NO 34
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(9)
<223> OTHER INFORMATION: All D-amino acids

<400> SEQUENCE: 34

Asp Val Asp Val Tyr Asp Asp Glu Asp
1               5

<210> SEQ ID NO 35
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(9)
<223> OTHER INFORMATION: All D-amino acids

<400> SEQUENCE: 35

Asp Val Asp Gly Tyr Asp Glu Glu Asp
1               5

<210> SEQ ID NO 36
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(9)
<223> OTHER INFORMATION: All D-amino acids

<400> SEQUENCE: 36
```

```
Asp Val Asp Glu Tyr Asp Asp Glu Asp
1               5

<210> SEQ ID NO 37
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(9)
<223> OTHER INFORMATION: All D-amino acids

<400> SEQUENCE: 37

Asp Ile Asp Glu Tyr Asp Asp Glu Asp
1               5

<210> SEQ ID NO 38
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(9)
<223> OTHER INFORMATION: All D-amino acids

<400> SEQUENCE: 38

Asp Leu Glu Glu Tyr Ile Asp Lys Asp
1               5

<210> SEQ ID NO 39
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(9)
<223> OTHER INFORMATION: All D-amino acids

<400> SEQUENCE: 39

Asp Val Asp Gly Tyr Asp Asp Glu Asp
1               5

<210> SEQ ID NO 40
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(11)
<223> OTHER INFORMATION: All D-amino acids

<400> SEQUENCE: 40

Lys Lys Ala Phe Pro Ala Ala Tyr Ile Ala Glu
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Synthesized
<220> FEATURE:
```

```
<221> NAME/KEY: MOD_RES
<222> LOCATION: (1)..(11)
<223> OTHER INFORMATION: All D-amino acids

<400> SEQUENCE: 41

Ser Met Arg Tyr Ile Asp Arg Asp Met Asp Phe
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(11)
<223> OTHER INFORMATION: All D-amino acids

<400> SEQUENCE: 42

Thr Asn Thr Tyr Ile Asp Arg Asp Met Asp Phe
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(11)
<223> OTHER INFORMATION: All D-amino acids

<400> SEQUENCE: 43

Ser Asp Arg Tyr Ile Asp Arg Asp Met Asp Phe
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(11)
<223> OTHER INFORMATION: All D-amino acids

<400> SEQUENCE: 44

Thr Asn Arg Tyr Ile Asp Arg Asp Met Asp Phe
1               5                   10

<210> SEQ ID NO 45
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(9)
<223> OTHER INFORMATION: All D-amino acids

<400> SEQUENCE: 45

Arg Arg Arg Gln Arg Arg Lys Lys Arg
1               5

<210> SEQ ID NO 46
```

```
<211> LENGTH: 36
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(11)
<223> OTHER INFORMATION: All D-amino acids
<220> FEATURE:
<221> NAME/KEY: MOD_RES
<222> LOCATION: (28)..(36)
<223> OTHER INFORMATION: All D-amino acids

<400> SEQUENCE: 46

Lys Lys Ala Phe Pro Ala Ala Tyr Ile Ala Glu Gly Gly Cys Gly Ala
1               5                   10                  15

Pro Thr Tyr Ser Pro Pro Pro Pro Gly Gly Arg Arg Arg Gln Arg
            20                  25                  30

Arg Lys Lys Arg
        35

<210> SEQ ID NO 47
<211> LENGTH: 37
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Biotinylated Lysine
<220> FEATURE:
<221> NAME/KEY: MOD_RES
<222> LOCATION: (2)..(11)
<223> OTHER INFORMATION: All D-amino acids
<220> FEATURE:
<221> NAME/KEY: MOD_RES
<222> LOCATION: (13)..(13)
<223> OTHER INFORMATION: Photo cleavable linker
<220> FEATURE:
<221> NAME/KEY: MOD_RES
<222> LOCATION: (28)..(37)
<223> OTHER INFORMATION: All D-amino acids

<400> SEQUENCE: 47

Lys Lys Lys Ala Phe Pro Ala Ala Tyr Ile Ala Glu Gly Gly Cys Gly
1               5                   10                  15

Ala Pro Thr Tyr Ser Pro Pro Pro Pro Gly Gly Arg Arg Arg Gln
            20                  25                  30

Arg Arg Lys Lys Arg
        35

<210> SEQ ID NO 48
<211> LENGTH: 13
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (12)..(12)
<223> OTHER INFORMATION: Biotinylated Lysine

<400> SEQUENCE: 48

Glu Ala Ile Tyr Ala Ala Pro Phe Ala Lys Lys Lys Gly
1               5                   10

<210> SEQ ID NO 49
```

```
<211> LENGTH: 13
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Biotinylated Lysine
<220> FEATURE:
<221> NAME/KEY: MOD_RES
<222> LOCATION: (2)..(12)
<223> OTHER INFORMATION: All D-amino acids

<400> SEQUENCE: 49

Lys Lys Lys Ala Phe Pro Ala Ala Tyr Ile Ala Glu Gly
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Synthesized

<400> SEQUENCE: 50

Ala Pro Thr Tyr Ser Pro Pro Pro Pro Pro Gly Gly
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(5)
<223> OTHER INFORMATION: All D-amino acids
<220> FEATURE:
<221> NAME/KEY: MOD_RES
<222> LOCATION: (11)..(12)
<223> OTHER INFORMATION: All D-amino acids

<400> SEQUENCE: 51

Ala Pro Thr Tyr Ser Pro Pro Pro Pro Pro Gly Gly
1               5                   10

<210> SEQ ID NO 52
<211> LENGTH: 36
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (12)..(12)
<223> OTHER INFORMATION: Biotinylated Lysine
<220> FEATURE:
<221> NAME/KEY: MOD_RES
<222> LOCATION: (12)..(12)
<223> OTHER INFORMATION: Photo cleavable linker

<400> SEQUENCE: 52

Glu Ala Ile Tyr Ala Ala Phe Lys Lys Gly Lys Gly Cys Gly Ala
1               5                   10                  15

Pro Thr Tyr Ser Pro Pro Pro Pro Gly Gly Arg Lys Lys Arg Arg
            20                  25                  30

Gln Arg Arg Arg
            35
```

```
<210> SEQ ID NO 53
<211> LENGTH: 26
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Biotinylated Lysine
<220> FEATURE:
<221> NAME/KEY: MOD_RES
<222> LOCATION: (2)..(12)
<223> OTHER INFORMATION: All D-amino acids
<220> FEATURE:
<221> NAME/KEY: MOD_RES
<222> LOCATION: (13)..(13)
<223> OTHER INFORMATION: Photo cleavable linker
<220> FEATURE:
<221> NAME/KEY: MOD_RES
<222> LOCATION: (18)..(26)
<223> OTHER INFORMATION: All D-amino acids

<400> SEQUENCE: 53

Lys Lys Lys Ala Phe Pro Ala Ala Tyr Ile Ala Glu Gly Gly Cys Gly
1               5                   10                  15

Gly Arg Arg Arg Gln Arg Arg Lys Lys Arg
            20                  25

<210> SEQ ID NO 54
<211> LENGTH: 26
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (13)..(13)
<223> OTHER INFORMATION: Biotinylated Lysine
<220> FEATURE:
<221> NAME/KEY: MOD_RES
<222> LOCATION: (13)..(13)
<223> OTHER INFORMATION: Photo cleavable linker

<400> SEQUENCE: 54

Glu Ala Ile Tyr Ala Ala Pro Phe Ala Lys Lys Gly Lys Gly Cys Gly
1               5                   10                  15

Gly Arg Lys Lys Arg Arg Gln Arg Arg
            20                  25
```